United States Patent [19]

Grimberg

[11] Patent Number: 4,764,374

[45] Date of Patent: Aug. 16, 1988

[54] PHARMACEUTICAL COMPOSITION BASED ON GUAR GUM AND OTHER ANTACIDS FOR PROTECTION OF THE OESOGASTRODUODENAL MUCOUS MEMBRANE

[76] Inventor: Georges S. Grimberg, 123 rue de l'Université, 75007 Paris, France

[21] Appl. No.: 836,475

[22] Filed: Mar. 5, 1986

[30] Foreign Application Priority Data

Mar. 6, 1985 [FR] France ................ 85 03306

[51] Int. Cl.$^4$ ............ A61K 33/42; A61K 33/06; A61K 33/08; A61K 31/715
[52] U.S. Cl. ............... 424/128; 424/154; 424/156; 424/157; 424/158; 514/54
[58] Field of Search .......... 424/157, 154, 156, 158, 424/128; 514/54

[56] References Cited

U.S. PATENT DOCUMENTS

| | | | |
|---|---|---|---|
| 3,415,927 | 12/1968 | Butensky et al. | 514/54 |
| 3,591,680 | 7/1971 | Green et al. | 424/156 |
| 3,984,571 | 10/1976 | Chen | 425/5 |
| 4,468,381 | 8/1984 | Mitra et al. | 424/158 |

FOREIGN PATENT DOCUMENTS

2033915  5/1980  United Kingdom ........ 424/157

OTHER PUBLICATIONS

*The Merck Index*, 9th ed., 4425, (1976), Merck & Co., Rahway, N.J.

*Primary Examiner*—Frederick E. Waddell
*Attorney, Agent, or Firm*—Browdy and Neimark

[57] ABSTRACT

The novel pharmaceutical composition is based on therapeutically active substances for protection of the oesogastroduodenal mucous membrane. There is used guar gum as a pH 1 to pH 0.8 antacid. Various other antacid agents are possibly added.

6 Claims, No Drawings

PHARMACEUTICAL COMPOSITION BASED ON GUAR GUM AND OTHER ANTACIDS FOR PROTECTION OF THE OESOGASTRODUODENAL MUCOUS MEMBRANE

OBJECT OF THE INVENTION

An object of the present invention is a novel pharmaceutical composition based on active therapeutical substances for protection of the oesogastroduodenal mucous membrane.

BACKGROUND OF THE INVENTION

In their conventional presentation, the protective compositions for the oesogastroduodenal mucous membrane are in different forms. They can for example be in suspension, granulates, tablets, powder. However in spite of these various presentations the result sought after is not reached since the purely physical phase is not always obtained and the dispersion is not good, which does not provide a good lining of the mucous membranes.

Moreover the various antacids used and their associations do not cover reasonably the various pH regions likely to appear in a patient.

SUMMARY OF THE INVENTION

According to the invention there is used, as a pH 1 to pH 0.8 antacid, guar gum to which can be added various other antacid agents.

According to another feature of the invention, the various antacids added to the guar gum are aluminum hydroxide, magnesium hydroxide, calcium carbonate and the corresponding oxides, as well as any other salts, oxides and hydroxides therapeutically active for protection of the oesogastroduodenal mucous membrane.

Various other features of the invention will become more apparent from the following detailed description.

DETAILED DESCRIPTION OF THE INVENTION

Hereafter are given several examples of the novel pharmaceutical composition from guar gum, aluminum hydroxide, Mg hydroxide and one or several active components which can also contain gelling agents, sweeteners and flavoring agents.

EXAMPLE 1

Ingestable pharmaceutical composition:
Aluminum hydroxide: 1,000 g
Guar gum in powder: 2,478 g
Silicone oil: 12.5 g
Sorbitan monooleate: 6.44 g
Polysorbate 80: 3.22 g
Micronized silica: 50 g
Sugar: 6,000 g
Sodium saccharinate: 10 g
Sodium cyclamate: 40 g
Coconut (aroma in powder): 200 g When the patient mixes the product thus obtained in an aqueous phase, the guar gum disperses and then swells, and at the moment of the swelling, captures the alumina hydroxide. This phenomenom continues in vivo.

It will be remarked in this example that the guar gum can be reduced in quantity and added notably with alginates, gelatine, gums and celluloses.

But it is remarkable to notice that the product obtained is in all cases of a fine aspect, produced rapidly and without irregularities. It can be easily conditioned and preserved in containers, with a view of its dispersion when used, or transformed into any convenient galenical form such as tablets, sachets, etc.

In all cases, if the present composition is dispersed in a liquid medium, for example water, whatever the proportions between the product and the water, the distribution will be rapidly obtained in the cold state, in a homogeneous way, without particular apparatus. The consistence of the gel obtained will vary with a given product, both with time and with the relative quantities of powder and water.

For so doing, it suffices to make up the mixture progressively and then to stir the mixture with a spoon or with the small measure used for metering the dose, until is obtained a first degree of gel thickening.

EXAMPLE 2

A pharmaceutical composition is practically identical if the 1,000 g of aluminum hydroxide are replaced by 500 g of aluminum hydroxide plus 500 g of magnesium hydroxide.

EXAMPLE 3

The antacid activity of the guar gum imparts the product with a very interesting activity. Actually, the hereabove cited examples show a very wide antacid activity zone.

The following formula enables to define four antacid activity zones:
(a) magnesium hydroxide: 0.5 g
(b) aluminum hydroxide: 0.5 g
(c) aluminum phosphate: 0.3 g
(g) guar gum (coated or not coated) 0.2 g
and three buffer power zones:
(a) from pH 3.5 to pH 3
(b) from pH 2 to pH 1.6
(c) from pH 1 to pH 0.8

The pH measuring technique is that of Vattier.

This composition has other advantages and, notably slow activity release kinetics: 30 minutes and even after this period there remains from 36 to 60% of activity according to the intervention pH.

To these four antacids can be associated various substances such as simethicone which has an excellent activity on meteorism and gases.

Various antacids can be associated with the guar gum.

The tests made on animals with the described formula have given excellent results and have shown for example that, with the rat as well as with the dog to which agents causing a quick ulceration of the gastric mucous membrane have been administered per os, a treatment of two or three weeks with the composition according to the invention led to a complete recovery or at least to a marked reduction of the ulcerations.

At present and although the clinical tests made on man are not complete, the composition according to the invention enables defining with precision, in more than 90% of the clinical cases observed, a quick and sometimes definitive amelioration of the portions of the oesogastroduodenal mucous membrane attacked.

In this respect, the composition of Example 3 has been found totally efficaceous on three patients to which Pentagastrine TM has been injected.

The composition of Example 3 enabled to treat two patents having hpersecretions of the gastric mucous corresponding to important hyperacidity.

The posology was three tablets a day during 15 days

What is claimed is:

1. A therapeutic method of treating excess gastrointestinal acidity and meteorism, comprising the step of administering a pharmaceutical composition comprising a therapeutically effective amount of guar gum to a patient in need of said therapy.

2. A method as set forth in claim 1, wherein said antacid comprises at least one other antacid agent in an amount effective as an antacid.

3. A method according to claim 2, wherein the other antacid agent is selected from the group consisting of aluminum hydroxide, magnesium hydroxide, calcium carbonate and corresponding oxides, as well as other salts, oxides and hydroxides therapeutically active for protection of the oesogastroduodenal mucous membrane.

4. A method as set forth in claim 2, wherein the antacid comprises the following formula per therapeutical dose:
   (a) guar gum: 0.2 g
   (b) magnesium hydroxide: 0.5 g
   (c) aluminum hydroxide: 0.5 g
   (d) aluminum phosphate: 0.3 g 5. A method as set forth in claim 1, wherein said antacid further comprises pharmaceutically acceptable excipients in excipiently effective amounts.

6. A method as set forth in claim 4, further comprising an amount of simethicone effective to significantly relieve meteorism.

* * * * *